(12) United States Patent
Nguyen (10) Patent No.: US 7,591,800 B2
(45) Date of Patent: Sep. 22, 2009

(54) NEEDLE PROTECTION DEVICE WITH DAMPENER

(75) Inventor: Steven Huu Nguyen, Keene, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 512 days.

(21) Appl. No.: 10/683,363

(22) Filed: Oct. 14, 2003

(65) Prior Publication Data

US 2004/0078007 A1   Apr. 22, 2004

Related U.S. Application Data

(62) Division of application No. 09/962,240, filed on Sep. 26, 2001, now Pat. No. 7,488,306.

(51) Int. Cl.
*A61M 5/00* (2006.01)
(52) U.S. Cl. ........................................ 604/110; 604/263
(58) Field of Classification Search ................ 604/110, 604/164.08, 192, 263; 128/919
See application file for complete search history.

(56) References Cited

U.S. PATENT DOCUMENTS

| 5,232,455 A | * | 8/1993 | Hollister | 604/192 |
| 5,277,311 A | * | 1/1994 | Hollister | 206/365 |
| 5,681,295 A | * | 10/1997 | Gyure et al. | 604/192 |
| 5,891,103 A | * | 4/1999 | Burns | 604/192 |
| 5,993,426 A | * | 11/1999 | Hollister | 604/192 |

\* cited by examiner

*Primary Examiner*—Nicholas D Lucchesi
*Assistant Examiner*—Victoria P Campbell
(74) *Attorney, Agent, or Firm*—Louis Woo (57) ABSTRACT

To prevent fluid collected at a contaminated needle from being splattered to the environment when the housing of a needle protection device is pivoted to enclose the needle, a bias member is provided in the needle protective housing to provide damping for the needle as the needle is moved within the housing. By damping the movement of the needle relative to the needle housing, splattering of the fluid that results from the jerky movements of the needle due to sudden acceleration/deceleration of the needle relative to the housing are absorbed and/or suppressed.

30 Claims, 5 Drawing Sheets

NEEDLE PROTECTION DEVICE WITH DAMPENER

This application is a divisional of prior application Ser. No. 09/962,240 filed Sep. 26, 2001 now U.S. Pat. No. 7,488,306.

FIELD OF THE INVENTION

The instant invention relates to needle safety devices and particularly a needle protection housing that is provided with a dampener that controls the movement and vibrations of a needle as the needle is being enclosed by the housing.

BACKGROUND OF THE INVENTION

For those needle protection devices that have a housing either hingedly or flexibly connected to a base to which a needle is matable or extends, when the needle sheath is pivoted to cover the needle, as the needle retaining mechanism for example a hook inside the needle sheath makes contact with the needle and then flexes over to grip the needle, the relative movement between the needle and the housing is interrupted abruptly so as to cause vibrations to the needle due to the sudden deceleration and then acceleration of the needle relative to the housing. This sudden deceleration/acceleration of the needle relative to the housing causes the needle to vibrate or jerk such that whatever fluid the needle has carried thereon is splattered to the environment or atomized to the atmosphere. Given that the fluid carried by the needle usually consists of blood which may well carry some contagious diseases such as the HIV virus, any excessive splattering, splashing or aerosolizing of the contaminated blood into the environment needs to be avoided. Accordingly, there is a need for a needle protection device, and more particularly the sheath or housing to the needle protection device, that has a feature that substantially prevents a needle from vibrating or jerking when it is being enclosed by the sheath.

In Hollister U.S. Pat. No. 5,993,426, there is disclosed a needle sheath that has fitted to the distal end thereof a material such as for example cotton that can absorb fluid collected at the tip of the needle cannula. The material that is fitted to the distal end of the needle sheath acts to absorb fluid that may be collected at the tip of the needle, before the needle makes contact with the needle retaining hook, so as to prevent the splattering of the fluid when the needle does make contact with the hook. One problem with the '426 device is that it is difficult to manufacture since the liquid absorbent material most likely needs to be hand fitted and glued to the distal end of the needle. The manufacturing cost for the device disclosed in the '426 patent may also be unacceptably high due to the additional expense of the absorbent material.

SUMMARY OF THE PRESENT INVENTION

The safety device of the instant invention is an improvement of any one of a series of Hollister U.S. patents assigned to the same assignee as the instant invention. These include: U.S. Pat. Nos. 4,982,842; 5,139,489; 5,154,285; 5,232,454; 5,232,455; 5,277,311.; 5,423,765; 5,993,426; RE37,110 and RE37,252. The respective disclosures of the aforenoted Hollister U.S. patents are incorporated by reference to the instant disclosure.

To overcome the potential splattering of contaminated fluid from a needle cannula, the cannula protective sheath or housing of the instant invention device is fitted with a non-needle retaining bias member that could be in the form of a leaf spring or a flexible flap or extension that extends, integrally or otherwise, from the back wall from the housing. The orientation and positioning of the bias member in the housing is such that when it makes contact with the needle, it would provide a biasing or dampening force against the needle and at the same time yield to the movement of the needle relative to the housing so that the needle is prevented from any sudden acceleration/deceleration movements when it makes contact with the needle retention mechanism in the protective sheath, or when a locking mechanism at the needle housing comes into contact and coacts with a matching locking mechanism at the base of the device and/or the needle hub of the needle assembly that is mated to the device.

It is therefore an objective the present invention to provide a needle safety device that prevents fluid collected at a contaminated needle from being splashed, splattered or aerosolized when the sheath of the device is pivoted to cover and then fixedly retain therein the-contaminated needle.

It is also an objective of the present invention to provide a simple to manufacture needle protection device that prevents fluid collected at a needle from splattering.

BRIEF DESCRIPTION OF THE FIGURES

The above mentioned objectives and advantages of the present invention will become apparent and the invention itself be best understood by reference to the following description of the present invention taken in conjunction with the accompanying drawings, wherein.

DETAILED DESCRIPTION OF THE INVENTION

In the aforenoted U.S. Pat. No. 4,982,842, an adapter for providing a safety needle sheath for housing a contaminated needle is disclosed. For illustration purposes, FIG. 1 is an improvement of the safety needle adapter disclosed in the '842 patent, although it should be appreciated that the improved needle protection sheath as disclosed in the instant invention is applicable to all of needle protective housings disclosed in all of the above noted incorporated by reference patents assigned to the assignee of the instant invention.

Figure 1:
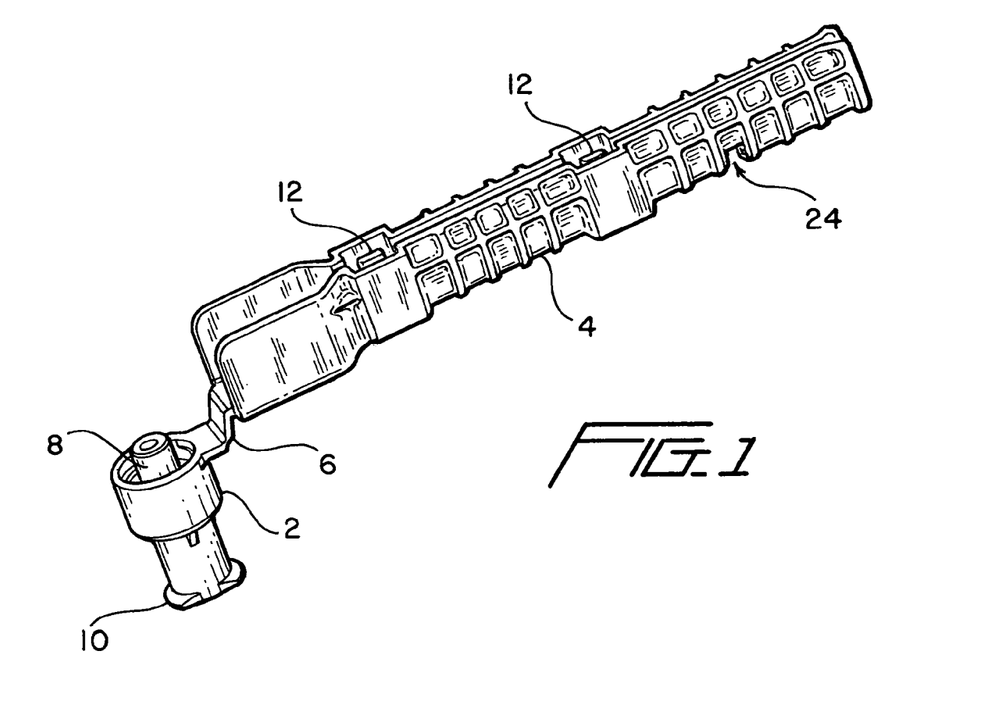
FIG. 1 is a perspective view of a safety device of the instant invention.

With reference to FIG. 1, a device similar to that disclosed in the '842 patent for accepting a needle is shown to have a base adapter 2 to which a housing 4 is connected by a living hinge 6. Note that housing 4 may also be connected to base 2 by means of a hinge or other pivoting mechanisms. Base 2 has a first luer end 8 for mating with the needle hub of a needle and a second luer end 10 for mating with a conventional syringe. As best shown in the semi-cut away view of FIG. 2 and the frontal view of FIG. 3, housing 4 has a number of needle grip means 12 in the form of hooks each having a lip 14 extending from the main body of hooks 12.

Figure 2:
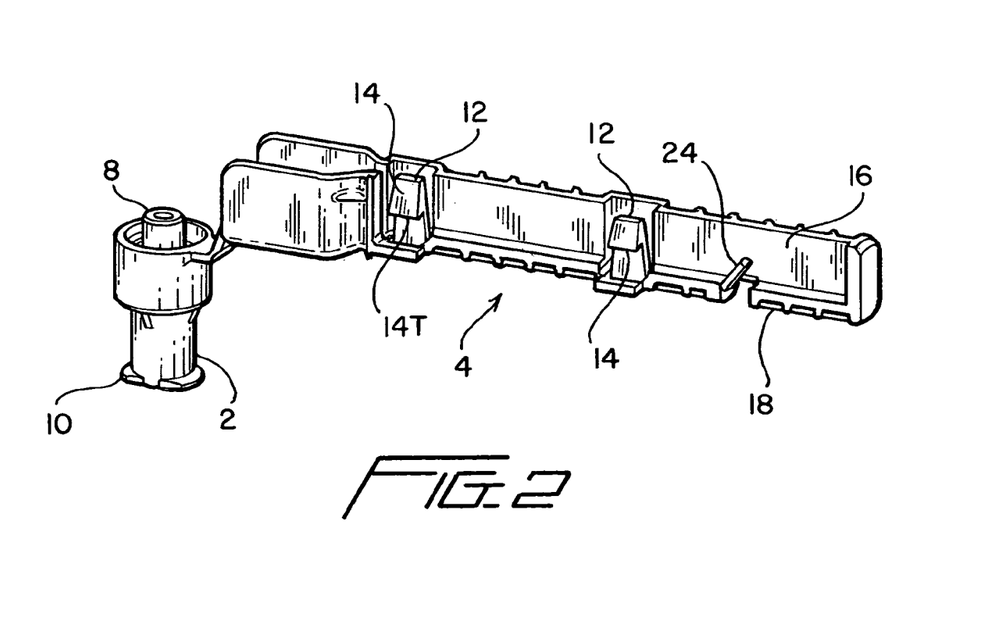
FIG. 2 is a semi-cut away perspective view of the FIG. 1 device illustrating in particular the inventive dampener.
Figure 3:
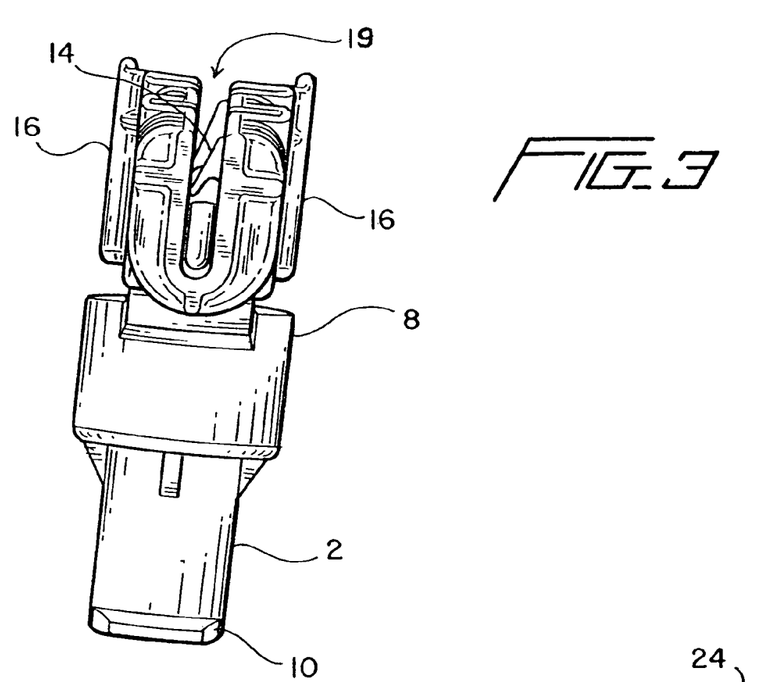
FIG. 3 is a frontal view of the device of FIG. 1 in which a viewer can look through the slot of the needle protection sheath or housing.
Figure 4:
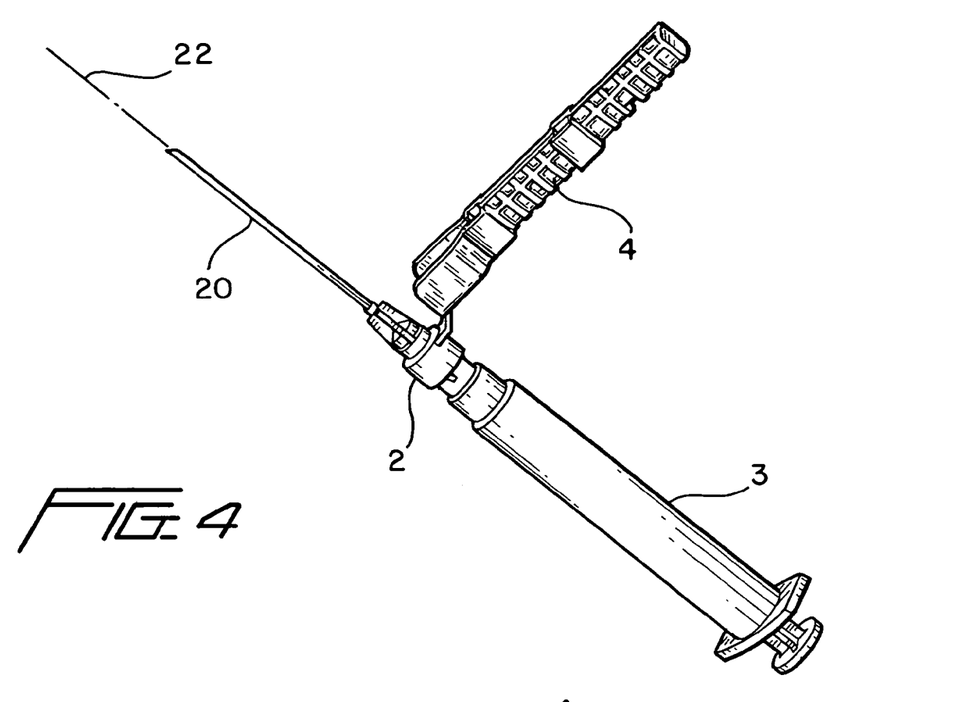
FIG. 4 is a perspective view illustrating the mating of the safety device of FIG. 1 to a syringe.

Housing 4 is comprised of two sidewalls 16 and a back wall 18, partially shown in FIG. 2. Due to the configuration of the extending sidewalls 16, a slot 19 runs longitudinally along the length of housing 4 to provide a passage wherethrough a needle cannula such as needle 20 shown in FIG. 4 passes, when housing 4 is pivoted towards the longitudinal axis 22 of base 2.

Prior to the instant invention, for the needle protection device such as that disclosed in the '842 patent, when housing 4 is pivoted to cover needle 20, as needle 20 comes into contact with lip 14, the relative movement of needle 20 is slowed, or decelerated. As the movement of needle 20 relative to housing 4 continues, the speed with which needle 20 moves continues to be slowed by lip 14 until needle 20 reaches tip 14t of lip 14, at which time the speed with which needle 20 moves relative to housing 4 increases due to the lack of contact with lip 14. In other Words, the movement of needle 20 relative to housing 4 is accelerated, thereby causing needle 20 to suddenly jerk forward. At the same time, lip 14, due to its inherent elasticity, returns to its original orientation, so as to snap over needle 20, which has moved beyond tip 14t. The snapping motion of lip 14 to needle 20 in turn causes needle 20 to vibrate, as needle 20 is caught by hook 12 and fixedly retained thereby in the recess of housing 4. Before the instant invention, the snap retention of needle 20 by hook 12, combined with the deceleration, sudden acceleration and stop movements of needle 20 relative to housing 4 cause needle 20 to vibrate or jerk to thereby splatter any fluid collected on needle 20.

To prevent such sudden jerky movements and vibrations in needle 20, the present invention incorporates into housing 4 a tongue or flap 24 that extends from back wall 18 at a given orientation. Although shown in FIG. 2 as extending from back wall 18 in a direction towards the distal end of housing 4, it should be appreciated that flap 24 may also be configured to extend from back wall 18 at location 19 in a direction where the tip of flap 24 is oriented or pointing towards the proximal end of housing 4. In other words, flap 24 could be oriented so as to face in either direction, for example forwardly as shown in FIG. 2, or backwardly.

For the embodiment shown in the figures, flap 24 is independently and flexibly integrated to back wall 18 and extends in such manner at an angle relative to the oncoming needle that it comes into contact with needle 20 after needle 20 has entered passageway 18 but before needle 20 has reached the position, or even comes into contact with lip 14, whereby it becomes fixedly retained by hooks 12 within housing 4. Flap 24 thereby acts as a dampener, or shock absorber, for needle 20 as the latter moves relative to housing 4, by damping the vibrations and jerky motions that needle 20 otherwise would experience due to the sudden deceleration/acceleration of its movement, as it enters into the recess of housing 4 and be fixedly retained therein, in this instance, by the hooks 12 in housing 4. As clearly shown in the figures and discussed above, flap 24 is independent of hooks 12 and does not retain needle 20. i.e., flap 24 is a non-needle retaining bias member as it is independent of any needle retaining mechanism and is therefore not adapted to retain needle 20.

Shock absorbing tongue 24 of the FIG. 2 embodiment extends from back wall 18 of housing 4 in a yieldingly bent manner so that when it comes into contact with needle 20, it is yieldingly moved by needle 20 towards back wall 18, and yet at the same time applies a biasing force to needle 20 to thereby smoothly damp the movement of needle 20. Thus, by modulating the speed with which needle 20 moves within housing 4, dampener flap 24 prevents the fluid collected on needle 20 from being splattered or aerosolized into the environment.

By integrating dampener 24 directly to housing 4, the manufacturing cost of providing such a biasing mechanism for housing 4 is de minimis. In place of an integrated dampener, a leaf spring with the same configuration may be press-fitted into the distal end of housing 4 to provide the same biasing damping force against needle 20. Although the cost for the fitting of such a leaf spring, be it metallic or plastic, is most likely higher than the integrated dampener shown in FIG. 2, the manufacturer cost for such hard-pressed leaf spring nonetheless is less than the manufacturing cost for the needle safety device disclosed in the aforenoted patent. As noted above, the dampener of the instant invention may be added to the needle protection housing of all of the aforenoted Hollister patents.

Figure 5:
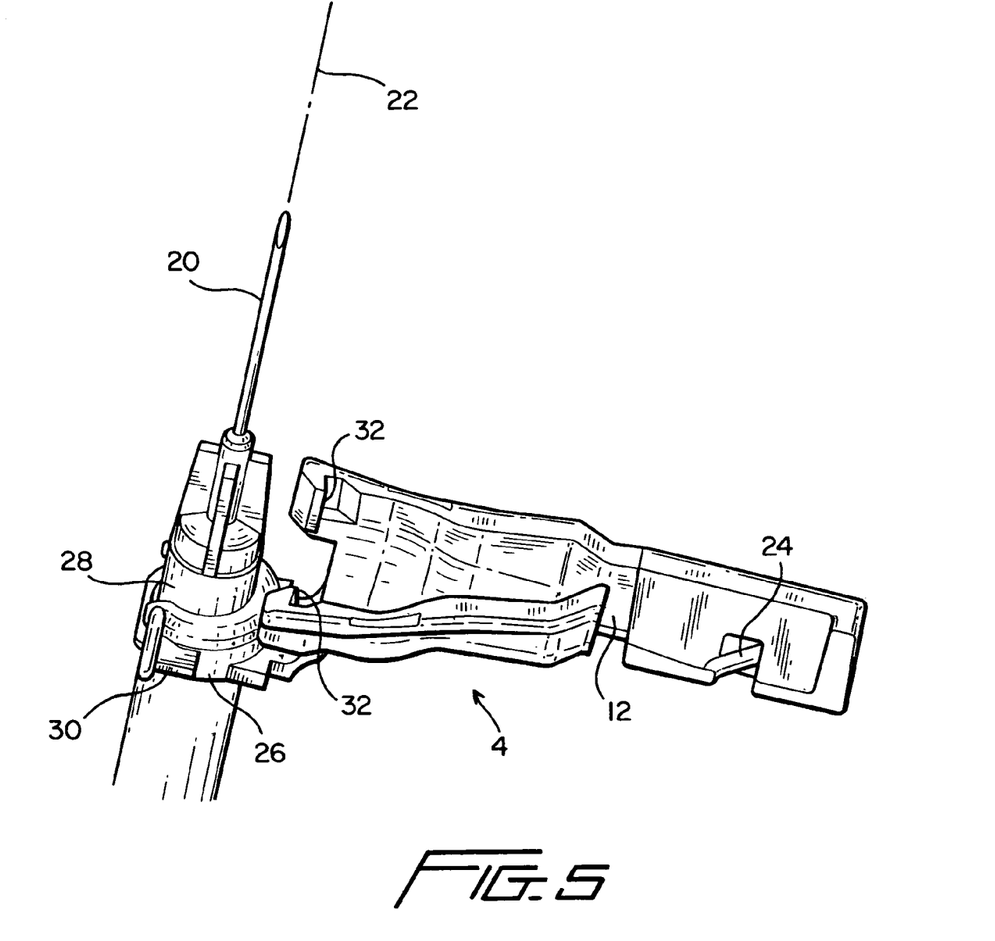
FIG. 5 is a perspective view of a second embodiment of the instant invention in which the inventive dampener is incorporated to a device disclosed in a co-pending application.
Figure 6:
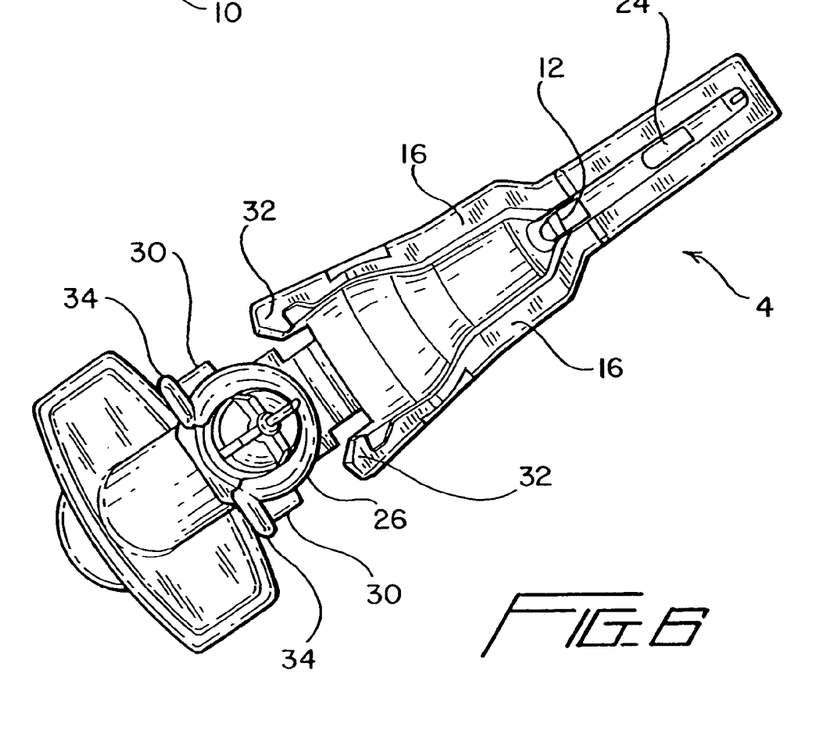
FIG. 6 is a top view of the FIG. 5 device.
Figure 7:
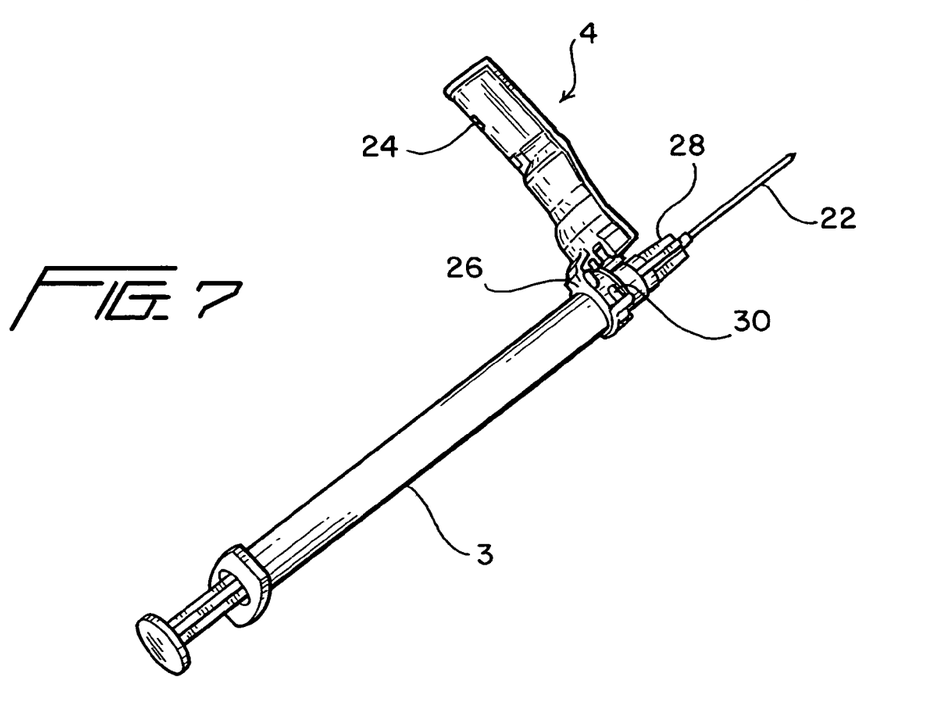
FIG. 7 is a perspective view illustrating the mating of the device of FIG. 5 with a syringe.

FIGS. 5, 6 and 7 illustrate the addition of the inventive dampener to the inventive needle protection device disclosed in copending application Ser. No. 09/883,360 filed Jul. 19, 2001. entitled "Needle Safety Device With Anti Removal Protection". The disclosure of the '360 application is incorporated by reference herein.

For the embodiment of the instant invention shown in FIGS. 5, 6 and 7, components the same as or similar to the earlier discussed components are numbered the same. As shown, the base of the needle protection device of the second embodiment is in the form of a collar 26 that fits about the hub 28 of a needle assembly, or the distal end of a syringe having an integrated hub to which a needle cannula 20 extends. Collar 26 has two ears 30 extending therefrom that coact with corresponding fingers 32 formed at the lower portion of each of the sidewalls 16 of housing 4. When housing 4 is pivoted toward needle 20 into substantial alignment along the longitudinal axis of needle 20, ears 30 and fingers 32 coact to fixedly retain housing 4 along the longitudinal axis 22, to thereby envelop needle 20 within housing 4. Two arms 34 formed at the respective ends of collar 26 prevent any tampering of the fixedly retained ears 30 and fingers 32. If desired, a hook 12 may also be provided integral of housing 4 to retainedly grasp needle 20.

To prevent needle 20 from vibrating due to the relative movement between it and housing 4, a tongue or flap 24 is provided at the distal end of housing 4 as in the previous embodiment so that a dampener is provided within housing 4. The operation of dampener 24 is as was discussed in the first embodiment so that, as housing 4 is pivoted toward the longitudinal axis 22 and fingers 32 coact with ears 30, as well as when needle 20 is grasped by hook 12 if hook 12 indeed is present, flap 24 acts as a dampener or shock absorber to modulate the movement of needle 20 relative to housing 4 to thereby substantially damp vibrations to needle 20 that result from housing 4 being snappedly locked to base 2, or needle 20 being snappedly gripped by hook 12. As shown, bias member 24 is oriented at a given angle with respect to the back wall of housing 4. Same as in the first embodiment, instead of an integral dampener, a leaf spring may be fitted to the distal end of housing 4.

Figure 8:
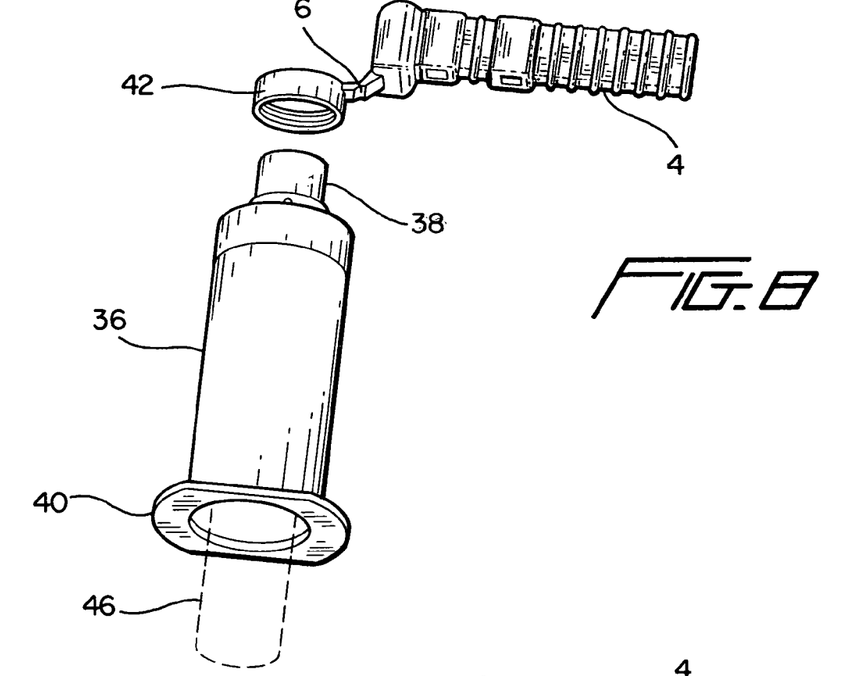
FIG. 8 is a perspective view of a Vacutainer holder to be fitted with the needle protection housing of the instant invention.
Figure 9:
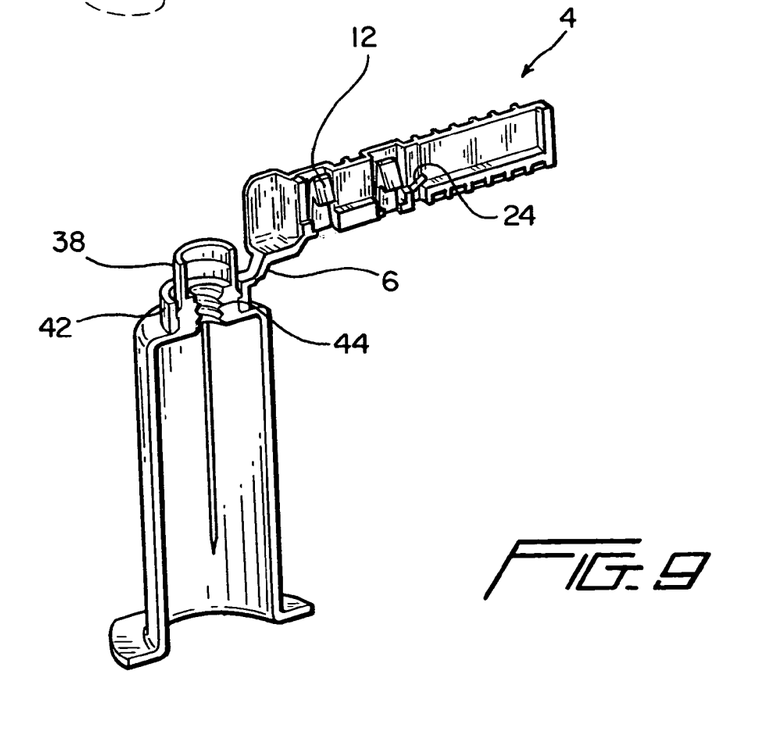
FIG. 9 is a semi-cut away perspective view of a Vacutainer holder fitted with the needle protection housing of the instant invention.

Yet another device fitted with a needle protection sheath having the inventive dampener is shown in FIGS. 8 and 9. In particular, FIG. 8 shows a Vacutainer holder 36 such as that disclosed in the aforenoted incorporated by reference Hollister U.S. Pat. No. 5,154,285. Holder 36 has one end 38 and another end 40. End 38, considered as the hub of holder 36, is rotatably fitted with a base 42, in the form of a collar, to which a housing 4 is attached by means of hinge 6. As disclosed in the '285 patent, hub 36 is adaptable to mate with a needle assembly that comprises a double-ended needle one of which extends from hub 38 while the other of which extends to the inside of holder 36. As is well known, the double-ended needle assembly has a threaded hub that threadingly mates to hub 38. The threads to which the hub of the double-ended needle assembly is mated in hub 36 is designated 44 in the semi-cut away perspective view of FIG. 9.

As best shown in FIG. 9, as with the embodiments discussed above, housing 4 fitted to the holder of FIGS. 8 and 9 likewise has integral hooks 12, as well as dampener 24. The respective operations of the needle gripping hooks 22 and dampener 24 are as were discussed with the earlier embodiments.

In operation, after a double-ended needle assembly is mated to hub 38, a vial or tube 46 for holding or collecting the fluid such as blood from the patient is inserted to end 40 of holder 36 so as to effect a fluid communication by means of the inward pointing needle of the double-ended needle. After the needle that is inserted into patient is withdrawn from the patient, housing 4 is pivoted via hinge 6 to a position substantially in alignment along the longitudinal axis of holder 36 so as to envelope the needle extending from hub 38, with hooks 12 eventually grasping the needle. As was discussed previously, dampener 24 prevents vibrations and jerky movements of the needle during the process which leads the needle becoming fixedly retained in housing 4.

Inasmuch as the present invention is subject to many variations, modifications and changes in detail, it is intended that all matter described throughout this specification and shown in the accompanying drawings be interpreted as illustrative only and not in a limiting sense. For example, a coil spring may be used in place of the above-disclosed leaf spring. Accordingly, it is intended that the instant invention be limited only by the spirit and scope by the hereto appended claims.

The invention claimed is:

1. A method of modulating movement of a needle entering into a needle protection housing pivotable relative to said needle for covering said needle, said housing having two side walls and a back wall, said method comprising the steps of:
    a) providing inside said housing a member independent of and not extending from either of said side walls and independent of any needle retaining mechanism for making contact with a portion of said needle after said portion of said needle enters into said housing through an open slot of said housing; and
    b) configuring said member to be yieldingly bent by said needle for dampening the movement of said needle as said needle moves within said housing and makes contact with said member.

2. Method of claim 1, wherein said housing comprises a needle grip means, said method further comprising the step of:
    positioning said member at a location within said housing to make contact with said needle after said needle enters into said housing but before said needle makes contact with said needle grip means within said housing so that said member would modulate the movement of said needle when said needle makes contact with said needle grip means.

3. Method of claim 1, wherein said needle extends from a needle hub, said method further comprising the step of:
    positioning said member at a location within said housing to make contact with said needle after said needle enters into said housing but before said housing makes contact with one locking means positioned relative to said needle hub that coacts with an other locking means at said housing so that said member would modulate the movement of said needle when said one and other locking means make contact with each other.

4. Method of claim 1, wherein said step a comprises the step of:
    flexibly integrating said member to said back wall of said housing.

5. Method of claim 1, wherein said step b comprises the step of:
    extending said member at an angle from said back wall of said housing with an end of said member away from said back wall being positioned within said housing at a location that comes into contact with said needle before said needle makes contact with any needle grip means within said housing or said housing coming into contact with any locking means outside of said housing.

6. Method of claim 1, wherein said member comprises a flap or tongue flexibly integrated to said back wall of said housing.

7. Method of claim 1, wherein said member comprises a leaf spring press fitted to said housing, said leaf spring extending at angle relative to said back wall of said housing.

8. Method of claim 1, wherein said housing comprises a base positioned relative to said needle, said method further comprising the steps of:
    providing at least one locking portion at said base; and
    providing at least an other locking portion at said housing so that said one locking portion coacts with said other portion to fixedly retain said housing to said base when said housing is moved relative to said needle to cover said needle.

9. method of claim 8, wherein said base comprises a collar and said needle extends from a needle hub, said method further comprising the step of:
    fitting said collar about said hub.

10. A method of dampening the movement of a needle entering a needle protection housing having needle secure means therein, said needle being mounted to a needle hub and said housing being pivotable relative to said needle hub from a position away from said needle to a position covering said needle, said housing having a proximal portion and a distal portion, said proximal portion being closer to said needle hub than said distal portion, said method comprising the steps of:
    a) providing a member within said housing at said distal portion independent of said needle secure means for making contact with a portion of said needle after said portion of said needle enters into said housing; and
    b) configuring said member to ensure said needle makes contact with said member prior to making contact with said needle secure means after said needle enters into said housing.

11. A method of modulating movement of a needle entering into a needle protection housing having a back wall and two side walls pivotable relative to said needle for covering said needle, said housing having a proximal portion and a distal portion, said method comprising the steps of:
    a) providing inside said housing a member independent of and not extending from either of said side walls and independent of any needle retaining mechanism for making contact with a portion of said needle after said portion of said needle enters into said housing through an open slot of said housing; and b) configuring said member to be yieldingly bent by said needle for dampening the movement of said needle as said needle moves within said housing and makes contact with said member.

12. method of claim 11, wherein said needle extends from a needle hub, said method further comprising the step of:
positioning said member at a location within said housing to make contact with said needle after said needle enters into said housing but before said housing makes contact with one locking means positioned relative to said needle hub that coacts with an other locking means at said housing so that said member would modulate the movement of said needle when said one and other locking means make contact with each other.

13. Method of claim 11, wherein said housing comprises a base positioned relative to said needle, said method further comprising the steps of:
providing at least one locking portion at said base; and
providing at least an other locking portion at said housing so that said one locking portion coacts with said other portion to fixedly retain said housing to said base when said housing is moved relative to said needle to cover said needle.

14. method of claim 13, wherein said base comprises a collar and said needle extends from a needle hub, said method further comprising the step of:
fitting said collar about said hub.

15. In combination, a needle hub having a needle extending therefrom, a housing having a proximal end pivotable relative to said needle hub, and needle retention means for fixedly retaining said needle within said housing when said housing is moved to a position substantially in alignment with said needle hub, a method of modulating the movement of said needle as said needle moves into said housing, comprising the steps of:
a) providing bias means independent of said needle retaining means within said housing at its distal end for making contact with a portion of said needle inside said housing when said housing is pivoted to be in alignment with said hub but before said needle makes contact with and is retained by said retaining means; and
b) configuring said bias means to be yieldingly moved by said needle and yet at the same time applying a bias force against said needle to thereby damp the movement of said needle.

16. A method of dampening the movement of a needle entering a needle protection housing having a back wall, two side walls and needle secure means, said needle being mounted to a needle hub and said housing being pivotable relative to said needle hub from a position away from said needle to a position covering said needle, said method comprising the steps of:
a) providing a member within said housing independent of and not extending from either of said two sidewalls and independent of said needle secure means for making contact with a portion of said needle after said portion of said needle enters into said housing; and
b) configuring said member to ensure said needle makes contact with said member prior to making contact with said needle secure means after said needle enters into said housing.

17. Method of claim 16, wherein said step a comprises the step of:
flexibly integrating said member to said back wall of said housing.

18. Method of claim 16, further comprising the step of:
extending said member at an angle from said back wall of said housing with an end of said member away from said back wall being positioned within said housing at a location that comes into contact with said needle before said needle makes contact with said needle secure means.

19. Method of claim 16, wherein said step b comprises the step of:
forming said member to be yieldingly bent by and yet at the same time applying a biasing force against said needle when said needle makes contact with said member to damp the movement of said needle.

20. Method of claim 16, wherein said member comprises a flap flexibly integrated to said back wall of said housing.

21. Method of claim 16, wherein said member comprises a leaf spring press fitted to said housing, said leaf spring extending at angle relative to said back wall of said housing.

22. Method of claim 16, wherein said needle hub extends from a syringe.

23. Method of claim 16, wherein said needle hub is connectable to a vacuum tube holder or a syringe.

24. In combination, a needle hub having a needle extending therefrom, a housing pivotable relative to said needle hub, and needle retention means for fixedly retaining said needle within said housing when said housing is moved to a position substantially in alignment with said needle hub, said housing having two side walls, a method of modulating the movement of said needle as said needle moves into said housing, comprising the steps of:
a) providing bias means within said housing independent of and not extending from either of said side walls and independent of said needle retention means for making contact with a portion of said needle inside said housing when said housing is pivoted to be in alignment with said hub but before said needle makes contact with and is retained by said retaining means;
b) configuring said bias means to be yieldingly moved by said needle and yet at the same time applying a bias force against said needle to thereby damp the movement of said needle.

25. Method of claim 24, wherein said step a comprises the step of:
flexibly integrating said bias means to said back wall of said housing.

26. Method of claim 24, wherein said step b comprises the step of:
extending said bias means at an angle from said back wall of said housing with a portion of said bias means being positioned within said housing at a location that comes into contact with said needle before said needle makes contact with said needle retention means.

27. Method of claim 24, wherein said bias means comprises a flap flexibly integrated to said back wall of said housing.

28. Method of claim 24, wherein said bias means comprises a leaf spring press fitted to said housing, said leaf spring extending at angle relative to said back wall of said housing.

29. Method of claim 24, further comprising the step of:
positioning said member relative to said back wall of said housing for contacting said needle after said needle enters into said housing and moves toward said back wall.

30. A method of modulating movement of a needle entering into a needle protection housing having a back wall pivotable relative to said needle for covering said needle, said method comprising the steps of:

a) integrating to the back wall of said housing at a given orientation relative to the back wall a tongue independent of any needle secure means that makes contact with said needle after said needle enters into said housing through an open slot of said housing; and b) configuring said tongue to be yieldingly moved by said needle for dampening the movement of said needle as said needle moves within said housing and makes contact with said tongue.

* * * * *